(12) United States Patent
Richardson et al.

(10) Patent No.: US 11,834,384 B2
(45) Date of Patent: Dec. 5, 2023

(54) PREPARATION OF OLEFIN BY ALCOHOL DEHYDRATION, AND USES THEREOF FOR MAKING POLYMER, FUEL OR FUEL ADDITIVE

(71) Applicant: TOTAL MARKETING SERVICES, Puteaux (FR)

(72) Inventors: Christine-Joy Richardson, Lyons (FR); Laurent Germanaud, Heyrieux (FR); Stéphane Kressmann, Communay (FR); Steven Henning, Downington, PA (US); Keith Nelson, Exton, PA (US); Delphine Minoux, Nivelles (BE)

(73) Assignee: TOTAL MARKETING SERVICES, Puteaux (FR)

( * ) Notice: Subject to any disclaimer, the term of this patent is extended or adjusted under 35 U.S.C. 154(b) by 0 days.

(21) Appl. No.: 16/979,620

(22) PCT Filed: Mar. 15, 2019

(86) PCT No.: PCT/EP2019/056557
§ 371 (c)(1),
(2) Date: Sep. 10, 2020

(87) PCT Pub. No.: WO2019/175393
PCT Pub. Date: Sep. 19, 2019

(65) Prior Publication Data
US 2021/0040012 A1 Feb. 11, 2021

(30) Foreign Application Priority Data

Mar. 16, 2018 (EP) .................................. 18305299
Feb. 11, 2019 (EP) .................................. 19305169

(51) Int. Cl.
*C07C 1/24* (2006.01)
*C07C 11/10* (2006.01)
*C07C 2/08* (2006.01)
*C08F 210/08* (2006.01)
*C10L 1/16* (2006.01)

(52) U.S. Cl.
CPC ............. *C07C 1/24* (2013.01); *C07C 2/08* (2013.01); *C08F 210/08* (2013.01); *C10L 1/1608* (2013.01); *C07C 11/10* (2013.01); *C07C 2521/04* (2013.01); *C07C 2529/65* (2013.01)

(58) Field of Classification Search
None
See application file for complete search history.

(56) References Cited

U.S. PATENT DOCUMENTS

| | | | |
|---|---|---|---|
| 3,932,537 A | 1/1976 | Wetzel et al. | |
| 4,303,555 A | 12/1981 | Boden et al. | |
| 4,359,412 A | 11/1982 | Boden | |
| 4,366,078 A | 12/1982 | Boden et al. | |
| 4,608,193 A | 8/1986 | Sprecker et al. | |
| 4,677,176 A | 6/1987 | Evans et al. | |
| 5,084,070 A * | 1/1992 | Kohler | C10L 1/023 44/449 |
| 5,166,455 A | 11/1992 | Chin et al. | |
| 5,221,776 A | 6/1993 | Alexander | |
| 5,243,121 A | 9/1993 | Madon et al. | |
| 5,656,698 A | 4/1997 | Hentges et al. | |
| 7,696,395 B2 | 4/2010 | Merrill | |
| 8,378,160 B2 | 2/2013 | Gruber et al. | |
| 2004/0122278 A1 | 6/2004 | Powers | |
| 2006/0030741 A1 | 2/2006 | Smith, Jr. et al. | |
| 2008/0306320 A1 | 12/2008 | Merrill | |
| 2009/0043144 A1 * | 2/2009 | Leyshon | C07C 11/18 585/671 |
| 2010/0022817 A1 | 1/2010 | Butler et al. | |
| 2010/0069542 A1 | 3/2010 | Gelbin et al. | |
| 2010/0216958 A1 * | 8/2010 | Peters | C08G 69/14 526/284 |
| 2012/0136190 A1 * | 5/2012 | Kaizik | C07C 1/24 585/640 |
| 2012/0157725 A1 | 6/2012 | McAuliffe | |
| 2017/0029668 A1 | 2/2017 | Nelson et al. | |

FOREIGN PATENT DOCUMENTS

| | | | | |
|---|---|---|---|---|
| EP | | 2 336 341 A1 | 6/2011 | |
| JP | | 7-223985 A | 8/1995 | |
| WO | WO 2009/079213 A2 | | 6/2009 | |
| WO | WO 2012/050658 A1 | | 4/2012 | |
| WO | WO 2012/052427 A1 | | 4/2012 | |
| WO | WO-2019097199 A1 * | | 5/2019 | ............. C10G 55/06 |

OTHER PUBLICATIONS

Montoya et al., Fusel Oil Separation Process, Conference Paper 2011 AIChE Annual Meeting, Oct. 2011, pp. 1-7. (Year: 2011).*
"New Route to Specialty Pyrethroid Olefin 3-Methyl-1-butene", Chem. Eng. News, Apr. 22, 1985, XP055483157, Retrieved from the Internet: URL:https://pubs.acs.org/doi/pdf/10.1021/cen-v063n016.p027 [retrieved on Jun. 12, 2018].
Antunes et al., "Alkenes oligomerization with resin catalysts," Fuel Processing Technology, vol. 138, 2015, pp. 86-99, 14 pages total.
González-rugerio et al., "TAEE synthesis from isoamylenes and ethanol by catalytic distillation: Pilot plant experiments and model validation," Fuel Processing Technology, vol. 102, 2012, pp. 1-10, 10 pages total.
International Preliminary Report on Patentability and English translation of the Written Opinion of the International Searching Authority for International Application No. PCT/EP2019/056557, dated Oct. 1, 2020.

(Continued)

*Primary Examiner* — Renee Robinson
(74) *Attorney, Agent, or Firm* — Birch, Stewart, Kolasch & Birch, LLP

(57) ABSTRACT

A process for the preparation of olefin by alcohol dehydration, for making polymer, fuel or fuel additive and use of olefin obtainable by said process for making polymer, fuel or fuel additive. Preferred olefin is $C_5$ olefin obtained from dehydration of an alcohol or alcohol mixture, preferably from fusel oil.

22 Claims, No Drawings

(56) References Cited

OTHER PUBLICATIONS

International Search Report for International Application No. PCT/EP2019/056557, dated May 15, 2019.
Izquierdo et al., "Fuel additives from glycerol etherification with light olefins: State of the art," Renewable and Sustainable Energy Reviews, vol. 16, 2012, pp. 6717-6724, 8 pages total.
Izquierdo et al., "New biodiesel additives from glycerol and isoamylenes," Biofuels, Bioproducts and Biorefining, vol. 8, 2014, pp. 658-669, 12 pages total.
Liu et al., "Methoxyl methyl ether isoamylene quercetin, a quercetin derivative, protects rat aorta endothelial cells against oxidation and apoptosis," Journal of Chinese Pharmaceutical Sciences, vol. 22, No. 4, 2013, pp. 355-360, 6 pages total.
Löning et al., "Dewatering of Solvent Mixtures—Comparison between Conventional Technologies and a New One," Chemical Engineering & Technology, vol. 24, 2001, pp. 242-245, 4 pages total.
Okafor et al., "Microreactor Performance Studies of the Cycloaddition of Isoamylene and α-Methylstyrene," Industrial & Engineering Chemistry Research, vol. 49, 2010, pp. 5549-5560, 12 pages total.
Soto et al., "Equilibrium of the simultaneous etherification of isobutene and isoamylenes with ethanol in liquid-phase," Chemical Engineering Research and Design, vol. 92, 2014, pp. 644-656, 13 pages total.
Vidal et al., "Biosynthesis of higher alcohol flavour compounds by the yeast *Saccharomyces cerevisiae*: impact of oxygen availability and responses to glucose pulse in minimal growth medium with leucine as sole nitrogen source," Centre for Strategic Technologies of the Northeast—CETENE, Oct. 2014, 28 pages total.
Wei et al., "The Coordination and Optimization Study of PSS Parameters of Multiple Generators," Advanced Materials Research, vols. 805-806, 2013, pp. 805-810, 7 pages total.
Yuan et al., "Engineering the leucine biosynthetic pathway for isoamyl alcohol overproduction in *Saccharomyces cerevisiae*," Journal of Industrial Microbiology & Biotechnology, Nov. 9, 2016, 11 pages total.
Office Action issued in Japanese Patent Application No. 2020-547417, dated Feb. 28, 2023.

* cited by examiner

PREPARATION OF OLEFIN BY ALCOHOL DEHYDRATION, AND USES THEREOF FOR MAKING POLYMER, FUEL OR FUEL ADDITIVE

BACKGROUND

Olefinic components are useful as reactants in oligomerization or polymerization reactions, as fuels or fuel components, as feedstock for hydrotreatment, etc. Olefins from $C_4$ to $C_{10}$ are particularly useful as monomers for oligomerization or polymerization or as fuel components, e.g. in petrol-type fuels.

$C_5$ olefins are used to prepare resins by copolymerization. Tackifying resins belong to a class of polymers that is characterized by low molecular weight, high glass transition temperature, and a roughly linear correlation of Tg to molecular weight in polymers of similar structure. These resins are made from copolymerization of styrene or derivative, a diene such as piperylene and a $C_5$ olefin. Preferred $C_5$ olefin is chosen among specific isomers of methylbutenes aka isoamylenes, namely 2-methyl-2-butene (2MB2) and 2-methyl-1-butene (2MB1).

2MB2 and 2MB1 (isoamylene isomers) are used in resin polymerization to control glass transition Temperature (Tg) and molecular weight due to their propensity for chain transfer. Their reactivity and chain transfer capability is a result of their branched olefin structure. 3-methyl-1-butene (3MB1), being a terminal non-branched olefin, is less capable in this capacity.

2MB2 and 2MB1 are usually produced by the deep catalytic cracking (DCC) of vacuum gas oil. DCC is similar to fluid catalytic cracking (FCC) and produces a higher yield of propylene, isobutylene, and isoamylene. With increased demand for propylene, DCC has grown in favor. Nonetheless, one could consider alternative methods to the production of branched $C_5$ olefins via dehydrogenation and/or isomerization of normal olefins and alkenes and the enzymatic conversion of hydroxyalkanoic acids.

Below are references for the production of isoamylenes and other $C_4$ and $C_5$ branched olefins, and their use:

U.S. Pat. No. 5,221,776 describes a catalyst for the isomerization of $C_5$ olefins to produce isoamylenes. U.S. Pat. No. 5,243,121 describes a fluid catalytic cracking process for increased production of isobutylene and isoamylenes. U.S. Pat. No. 5,166,455 describes a process for converting $C_5$-$C_7$ olefins (e.g. FCC light naphtha) to isobutene- and isoamylene-rich streams. WO 2012052427A1 describes the production of alkenes by the combined enzymatic conversion of 3-hydroxyalkanoic acids using different mevalonate pyrophosphate decarboxylases.

U.S. Pat. No. 8,378,160 describes a process for preparing a hydrocarbon olefin composition from a feedstock derived from biomass. The process includes dehydrating isobutanol to obtain a $C_4$ olefin, which is then oligomerized to form dimers and trimers.

2MB2 is most commonly used as a starting material for other products as opposed to being used as is for some final applications. While not an exhaustive one, the public literature reveals several uses for isoamylene. These include (i) hydrocarbon resin modification (softening point/Tg/molecular weight control), (ii) fuel additives via oligomerization (typically dimerization) for octane boosters or via etherification with methanol or ethanol, (iii) synthetic building block such as precursor to diolefins, flavor/fragrance enhancers, antioxidants, typically alkyl phenols, or as synthon for fine chemicals or pharmaceutical ingredients preparation.

With regards to hydrocarbon Resin Modification, WO 2012050658A1 describes the use of isoamylene to control softening point and molecular weight (Mz) in the synthesis of hydrocarbon resins, U.S. Pat. No.5,656,698 describes use in the synthesis of hydrocarbon tackifying resins, U.S. Pat. No. 4,677,176 also describes use in the synthesis of hydrocarbon tackifying resins.

As per fuel additive, US 20120157725A1 describes the partial hydrogenation of isoprene to a mixture of isoamylenes which can be reacted with alcohols to afford oxygenates such as Tert-Amyl Methyl Ether (TAME), acid catalytically dimerized, or reacted with HF to produce high octane alkylates. Fuel Processing Technology (2015)138, 86-99 describes the use of cationic exchange resins for the oligomerization of isoamylene for production of octane boosters. Biofuels, Bioadditives & Biorefining (2014), 8(5), 658-669 describes the catalytic etherification of glycerol (a byproduct of biodiesel production) and isoamylenes to produce oxygenated fuel additives. Advanced Material Research (Durnten-Zurich, Switzerland) (2013), 805-806 describes catalysts for the etherification of isoamylene and methanol. Chemical Engineering Research and Design (2014), 92(4), 644-656 describes catalysts for the simultaneous etherification of isobutene and isoamylenes with ethanol. Renewable & Sustainable Energy Reviews (2012), 16(9), 6717-6724 is a review of methods for the etherification of glycerol with light olefins such as isobutene and isoamylenes. Fuel Processing Technology (2012), 102, 1-10 describes the synthesis of tert-amyl ethyl ether (TAEE) from isoamylene and ethanol. US 20060030741 describes a process for the etherification of $C_4$, $C_6$, and/or $C_6$ iso-olefins.

As synthetic precursor to diolefins building block, US 20080306320A1/U.S. Pat. No. 7,696,395B2 (Fina Technology) describes a method for the dehydrogenation of isoamylene to make isoprene, and US 20100022817 describes the dehydrogenation of hydrocarbons to alkenes, e.g. n-pentene to piperylene, n-butane to butadiene, and isoamylene to isoprene.

As synthetic flavor and fragrance enhancer building block, U.S. Pat. No. 4,366,078 (International Flavors and Fragrances) describes the dimerization of isoamylene to form diisoamylene mixture that is used as an aroma enhancer. U.S. Pat. No. 4,608,193 claims isochroman derivatives made from alpha methylstyrene and isoamylene as aroma potentiators in perfumes. U.S. Pat. No. 4,359,412 describes the production of C11 acetates used as flavoring agents via isoamylene dimerization. Reaction of the product with formaldehyde via the Prins reaction is followed by acetylation by treatment with acetic anhydride. U.S. Pat. No. 4,303,555 describes the production of isoamylene dimers for enhancing or augmenting the aroma of perfumes or colognes. Industrial & Engineering Chemistry Research (2010), 49(12), 5549-5560 describes the cycloaddition of isoamylene and alpha methylstyrene to form 1,1,2,3,3-pentamethylindane, an intermediate in the synthesis of musk fragrances.

As antioxidant, U.S. Pat. No. 3,932,537 describes a method for the alkylation of phenol with isobutylene or isoamylene. JP 07223985 describes the preparation of 2-methyl-6-tert-amyl phenol via reaction of cresol with isoamylene. The product is an intermediate for phenolic antioxidants. U.S. Pat. No. 20100069542 describes use of amylene to synthesize liquid amylaryl phosphites that are then used as stabilizers in various polymers.

Other uses of isoamylenes are described in the following papers: Polymer Preprints (ACS, Division of Polymer Chemistry) (1999), 40(2), 786-787 discusses the use of isoamylene in the synthesis of anionic initiators. J. of Chinese Pharmaceutical Sciences (2013), 22(4), 355-360 describes the synthesis of methoxy methyl ether isoamylene quercetin (MIAQ) that are useful in assisting the healing of injured rat aorta endothelial cells. Chemical Engineering & Technology (2001), 24(3), 242-245 describes the dewatering of chloroform by the catalytic conversion of isoamylene to isoamyl alcohol.

Albeit isoamylenes are commercially available, cheaper alternative sources as well as alternative tackifying polymers obtained thereof are desirable.

SUMMARY

The present invention is directed to a process for the preparation of a $C_5$ olefin mixture containing (i) at least 5 wt % of an olefin mixture comprising (i-a) 2-methyl-but-2-ene, (i-b) 2-methyl-but-1-ene and (i-c) 3-methyl-but-1-ene, and optionally (ii) (ii-a) one $C_4$ olefin chosen among 1-butene, 2-butene, 2-methylpropene, and/or (ii-b) one $C_6$ olefin chosen among 1-hexene, 2-hexene, 3-hexene, 2-methyl-1-pentene, 3-methyl-1-pentene, 4-methyl-1-pentene, 2-ethyl-1-butene, 2,3-dimethyl-1-butene, 2,3-dimethyl-2-butene, cyclohexene, 2-methyl-2-pentene, 3-methyl-2-pentene, 3,3-dimethyl-1-butene, 1-methyl-cyclopentene, 3-methyl-cyclopentene, 4-methyl-cyclopentene, methylene-cyclopentane, and/or (ii-c) one $C_{15}$ hydrocarbon, said process comprising the steps of:
  a) providing an initial composition comprising at least 20 wt % of $C_5$ branched alcohol based on the total weight of the initial composition, and
  b1) dehydrating the initial composition and separating the obtained dehydrated composition to provide a first stream enriched in $C_2$ olefins, a second stream enriched in $C_5$ olefins, and a third stream containing heavier compounds, the $C_5$ olefin mixture being recovered from the second stream enriched in $C_5$ olefins, or
  b2) separating the initial composition to provide a first stream enriched in $C_2$ alcohols, a second stream enriched in $C_5$ alcohols, and a third stream enriched in heavier compounds, and dehydrating the second stream enriched in $C_5$ alcohols to obtain the $C_5$ olefin mixture.

The present invention is also directed to a $C_5$ olefin mixture which can be obtained from the process of the invention, said $C_5$ olefin mixture containing (i) at least 5wt % of an olefin mixture comprising (i-a) 2-methyl-but-2-ene, (i-b) 2-methyl-but-1-ene and (i-c) 3-methyl-but-1-ene, and optionally (ii) (ii-a) one $C_4$ olefin chosen among 1-butene, 2-butene, 2-methylpropene, and/or (ii-b) one $C_6$ olefin chosen among 1-hexene, 2-hexene, 3-hexene, 2-methyl-1-pentene, 3-methyl-1-pentene, 4-methyl-1-pentene, 2-ethyl-1-butene, 2,3-dimethyl-1-butene, 2,3-dimethyl-2-butene, cyclohexene, 2-methyl-2-pentene, 3-methyl-2-pentene, 3,3-dimethyl-1-butene, 1-methyl-cyclopentene, 3-methyl-cyclopentene, 4-methyl-cyclopentene, methylene-cyclopentane, and/or (ii-c) one $C_{15}$ hydrocarbon, that may be used :
  for making an oligomer or a polymer, or
  as fuel or fuel additive.

DETAILED DESCRIPTION

According to a first aspect, the instant invention is directed to a process for the preparation of a $C_5$ olefin mixture containing (i) at least 5 wt % of an olefin mixture comprising (i-a) 2-methyl-but-2-ene, (i-b) 2-methyl-but-1-ene and (i-c) 3-methyl-but-1-ene, and optionally (ii) (ii-a) one $C_4$ olefin chosen among 1-butene, 2-butene, 2-methylpropene, and/or (ii-b) one $C_6$ olefin chosen among 1-hexene, 2-hexene, 3-hexene, 2-methyl-1-pentene, 3-methyl-1-pentene, 4-methyl-1-pentene, 2-ethyl-1-butene, 2,3-dimethyl-1-butene, 2,3-dimethyl-2-butene, cyclohexene, 2-methyl-2-pentene, 3-methyl-2-pentene, 3,3-dimethyl-1-butene, 1-methyl-cyclopentene, 3-methyl-cyclopentene, 4-methyl-cyclopentene, methylene-cyclopentane, and/or (ii-c) one $C_{15}$ hydrocarbon, said process comprising the steps of:
  a) providing an initial composition comprising at least 20 wt % of $C_5$ branched alcohol based on the total weight of the initial composition, and
  b1) dehydrating the initial composition and separating the obtained dehydrated composition to provide a first stream enriched in $C_2$ olefins, a second stream enriched in $C_5$ olefins, and a third stream containing heavier compounds, the $C_5$ olefin mixture being recovered from the second stream enriched in $C_5$ olefins, or
  b2) separating the initial composition to provide a first stream enriched in $C_2$ alcohols, a second stream enriched in $C_5$ alcohols, and a third stream enriched in heavier compounds, and dehydrating the second stream enriched in $C_5$ alcohols to obtain the $C_5$ olefin mixture.

Preferably, and according to the first aspect of the invention, the $C_5$ olefin mixture containing (i) at least 5 wt % of an olefin mixture (i-a) 2-methyl-but-2-ene, (i-b) 2-methyl-but-1-ene and (i-c) 3-methyl-but-1-ene, further comprises (i-d) cis-2-pentene and/or trans-2-pentene.

Initial Composition

The initial composition preferably comes from fermentation of a biomass feedstock, e.g. a feedstock of biological origin preferably chosen from sugars and sugar precursors such as cellulose, hemicellulose, lignocellulose, and mixtures thereof. Alcohols may also be obtained by biological transformation of feedstocks by microalgae or microorganisms such as yeast and bacteria. Some yeast can produce the preferred alcohols in major amounts as described in "Biosynthesis of higher alcohol flavour compounds by the yeast *Saccharomyces cerevisiae*: impact of oxygen availability and responses to glucose pulse in minimal growth medium with leucine as sole nitrogen source" by Esteban Espinosa Vidal, Marcos Antonio de Morais Jr, Jean Marie Francois and Gustavo M. de Billerbeck published in *Yeast* 2015; 32: 47-56 or "Engineering the leucine biosynthetic pathway for isoamyl alcohol overproduction in *Saccharomyces cerevisiae*" by Yuan J, Mishra P and Ching CB published in *J Ind Microbiol Biotechnol*. 2017 Jan.; 44(1):107-117.

According to a preferred embodiment, the initial composition is produced by sugar fermentation, such sugar advantageously coming from cane or beetroot. Preferred sugar is saccharose, glucose, fructose, maltose and their mixtures and isomers.

The initial composition is advantageously an alcohol mixture from fermentation coming from raw or refined fusel oil, preferably a $C_{4+}$ or $C_4$-$C_6$ cut, more preferably a $C_5$ cut isolated from fusel oil. Raw fusel oil corresponds to the distillation bottoms of ethanol produced by fermentation of biomass, such as sugar cane, sugar beetroot, potatoes or any other vegetal source that is susceptible to produce alcohols by fermenting. Fusel oil is well known in the art and comprises a mixture of light alcohols, fatty esters, terpenes and furfural. The alcohols comprised in fusel oil are mainly propanol, butanol, amyl alcohol, isoamyl alcohols and hexanol and optionally heavier linear alcohols such as $C_7$ or $C_8$ alcohols. A $C_{4+}$ cut here corresponds to a composition essentially comprising molecules having 4 or more carbon atoms within their backbone. For instance, 1-butanol, 2-methyl-1-propanol, 3-methylbutan-2-ol, ethyl-pentanoate are molecules comprising respectively 4, 4, 5 and 7 carbon atoms.

Fusel oil may be obtained by several processes well known from the skilled person, e.g. by direct removal in the distillation column and cooling. The removed fraction can be purified e.g. by extraction and decantation. A liquid/liquid extraction by addition of water followed by a decantation leads to the formation of two phases. The upper phase comprises mainly amyl and butyl alcohols, slightly soluble in water. It is named settled fusel oil or raw fusel oil and can be chemically treated, usually by a salt saturated solution and/or fractionated by distillation to remove water and residual ethanol. A refined fusel oil is thus obtained. The various fractions of fusel oil may also be separated by using adsorbents, which are regenerated thereafter. Among the tested adsorbents, granulated vegetal activated charcoal is preferred since it is able to adsorb eight times its weight of fusel oil.

According to a preferred embodiment, $C_5$ branched alcohol present in the initial composition is isoamyl alcohol, i.e. 3-methylbutan-1-ol and 2-methylbutan-1-ol.

According to a preferred embodiment, the initial composition comprises at least 30 wt %, preferably at least 40 wt %, more preferably at least 50 wt %, more preferably at least 60 wt %, even more preferably at least 70 wt % $C_5$ branched alcohols, based on the total weight of the composition.

$C_4$ alcohols may also be present in the initial composition, among which butan-1-ol and 2-methylpropan-1-ol. The initial composition may comprise one of these $C_4$ alcohols or both.

$C_3$ alcohols may also be present in the initial composition, among which propan-1-ol also known as n-propanol. The initial composition may comprise 0.01 to 20 wt % of $C_3$ alcohol, preferably 0.5 to 10 wt %, and preferentially 1 to 5 wt %, based on the total weight of the initial composition.

According to a preferred embodiment, the initial composition comprises at least 20 wt % $C_5$ branched alcohols, at least 1 wt % ethanol, at least 0.1 wt % n-propanol, at least 1 wt % $C_4$ alcohols, at most 1.5 wt % esters and at least 5 wt % water, based on the total weight of the initial composition.

According to a preferred embodiment, the initial composition comprises at least 20 wt % $C_5$ branched alcohols, at least 1 wt % ethanol, at least 1 wt % n-propanol, at least 2 wt % $C_4$ alcohols, at most 1% esters and at most 10 wt % water, based on the total weight of the initial composition.

Dehydration Step

According to a preferred embodiment, the dehydration step is carried out in the presence of a dehydration catalyst, containing zeolites having preferably the MFI, MTT, FER, MEL, TON, MWW, EUO, MFS structure; alumina, silica-alumina and alumino silicate. The dehydration catalyst is preferably chosen from gamma-alumina, H-ZSM-5, H-FER, phosphorous containing ZSM-5 or any mixture thereof. An example of gamma-alumina is the brand range PurAl® commercialized by Sasol.

According to an advantageous embodiment, the catalyst is a gamma-alumina, preferably gamma-alumina extrudates of 1.2 mm having the following structural characteristics: specific surface of 200 m²/g, distribution centered around 124 Å and pore volume of 0.588 mL/g.

According to another advantageous embodiment, the catalyst is a ferrierite catalyst, preferably a zeolite ammonium ferrierite powder or in the form of extrudates (Zeolyst, CP914 CYL-1.6).

The dehydration step can be made by a continuous process in a fixed bed. It is generally operated in gaseous phase.

During the dehydration process, the product to dehydrate is contacted with the catalyst, preferably at a temperature between 100 and 700° C., more preferably between 200 and 600° C., even more preferably between 300 and 500° C., at a pressure lower than or equal to 10 bar, preferably lower than or equal to 5 bar, and more preferably at atmospheric pressure (around 1 to 2 bar).

According to a preferred embodiment, the Weight Hourly Space Velocity WHSV during the dehydration is between 1 and 10 $h^{-1}$, preferably between 2 and 8 $h^{-1}$.

During the dehydration step, at least part of the alcohols present in the product to dehydrate is converted to olefins, and the non-converted alcohols fraction may be separated and recycled into the feed.

According to a preferred embodiment (step b1) of the process of the invention), the dehydration step is carried out before the separation step.

According to this embodiment, the dehydration is operated on the initial composition as defined in the present invention and the obtained dehydrated composition comprises, based on the total weight of the dehydrated composition, at least 5 wt % 2-methyl-but-2-ene, at least 5 wt % 2-methyl-but-1-ene and at least 2 wt % 3-methyl-but-1-ene.

According to a preferred embodiment, the dehydration is operated on the initial composition as defined in the present invention and the obtained dehydrated composition comprises, based on the total weight of the dehydrated composition, at least 5 wt % 2-methyl-but-2-ene, at least 5 wt % 2-methyl-but-1-ene, at least 2 wt % 3-methyl-but-1-ene, and optionally 0.1 to 10 wt % $C_2$ compounds, 0.1 to 10 wt % of $C_3$ compounds, at least 2 wt % of $C_4$ compounds and optionally $C_5$ alcohols as well as water.

According to this embodiment, the $C_2$ compounds may be alcohols and/or olefins comprising 2 carbon atoms, the $C_3$ compounds may be alcohols and/or olefins comprising 3 carbon atoms and the $C_4$ compounds may be alcohols and/or olefins comprising 4 carbon atoms.

Separation Step

The dehydration step is preceded or followed by a separation step. Said separation step enables to obtain a first stream enriched in $C_2$ compounds, a second stream enriched in $C_5$ compounds and a third stream containing heavier compounds.

By "stream enriched in $C_n$ compound" is meant, according to the present invention, that the mass proportion of said $C_n$ compound in said stream after separation is greater than the mass proportion of said $C_n$ compound in the product to separate.

By "$C_n$ compound" is meant, according to the present invention, a "$C_n$ olefin" and/or a "$C_n$ alcohol".

By "$C_n$ olefin" is meant, according to the present invention, an olefin having n carbon atoms.

By "$C_n$ alcohol" is meant, according to the present invention, an alcohol having n carbon atoms.

According to a preferred embodiment, the separation step is made by distillation.

In a first embodiment (step b1) of the process of the invention), the separation step follows the dehydration step. In this embodiment, the separation step enables to obtain:

a first stream enriched in $C_2$ hydrocarbons, mainly ethylene and optionally $C_3$ hydrocarbons, mainly propylene, a second stream enriched in $C_5$ olefins and optionally $C_4$ olefins and/or $C_6$ olefins, and a third stream containing compounds heavier than $C_6$ olefins and optionally esters, $C_4$ alcohols and/or $C_5$ alcohols In this embodiment, the second stream comprises preferably at least 50 wt % $C_5$ olefins comprising 3-methyl-but-1-ene, 2-methyl-but-2-ene and 2-methyl-but-1-ene based on the total weight of the second stream.

In this embodiment, the second stream comprises preferably at least 50 wt %, more preferably at least 60 wt %, preferentially at least 70 wt % $C_5$ olefins comprising 3-methyl-but-1-ene, 2-methyl-but-2-ene and 2-methyl-but-1-ene based on the total weight of the second stream.

In this embodiment, the $C_5$ olefin mixture is recovered from the second stream enriched in $C_5$ olefins and optionally $C_4$ olefins and/or $C_6$ olefins.

In a second embodiment (step b2) of the process of the invention), the separation step precedes the dehydration step. In this embodiment, the separation step enables to obtain:

a first stream enriched in ethanol and optionally $C_3$ alcohols, a second stream enriched in $C_5$ alcohols and optionally $C_4$ alcohols and optionally $C_6$ alcohols, and a third stream containing compounds heavier than $C_6$ alcohols and optionally, esters In this embodiment, the dehydration step is made on the second stream.

In this embodiment, the second stream comprises preferably at least 50 wt % $C_5$ branched alcohols, based on the total weight of the second stream.

In this embodiment, the second stream comprises preferably at least 50 wt %, more preferably at least 60 wt %, preferentially at least 70 wt % $C_5$ branched alcohols chosen from 3-methylbutan-1-ol, 2-methylbutan-1-ol, and mixtures thereof, based on the total weight of the second stream.

According to a particular embodiment, the first stream is enriched in ethanol, n-propanol, isopropanol and optionally water and esters.

According to a second aspect, the instant invention is directed to the use of a $C_5$ olefin mixture which can be obtained from the process of the invention, for making an oligomer or a polymer, or as fuel or fuel additive, said $C_5$ olefin mixture containing (i) at least 5wt % of an olefin mixture comprising (i-a) 2-methyl-but-2-ene, (i-b) 2-methyl-but-1-ene and (i-c) 3-methyl-but-1-ene, and optionally (ii) (ii-a) one $C_4$ olefin chosen among 1-butene, 2-butene, 2-methylpropene, and/or (ii-b) one $C_6$ olefin chosen among 1-hexene, 2-hexene, 3-hexene, 2-methyl-1-pentene, 3-methyl-1-pentene, 4-methyl-1-pentene, 2-ethyl-1-butene, 2,3-dimethyl-1-butene, 2,3-dimethyl-2-butene, cyclohexene, 2-methyl-2-pentene, 3-methyl-2-pentene, 3,3-dimethyl-1-butene, 1-methyl-cyclopentene, 3-methyl-cyclopentene, 4-methyl-cyclopentene, methylene-cyclopentane, and/or (ii-c) one $C_{15}$ hydrocarbon.

Unexpectedly, it has been found that the above-mentioned $C_5$ olefins mixture could be efficiently obtained by dehydration of alcohols using proper dehydration catalyst. In addition, resulting $C_5$ olefin mixture has been found to be appropriate for making a polymer or to be used as fuel or fuel additive.

The term "essentially all", as present in this document and unless otherwise specified, means more than 80% of the identified subject matter to which it refers, preferably more that 90%, more preferably more than 95%, and even more preferably more than 98% of the subject matter to which it refers. When the term "essentially all" directly refers to a product or a composition, percentage is weight percent (wt %).

Above-mentioned $C_{4+}$ cut can be obtained by distillation of fusel oil until all or essentially all of $C_3$ containing products and lighter products are evaporated from the fusel oil.

Preferably, the $C_5$ olefin mixture can be used for making an oligomer or a polymer by combining, in the presence of a catalyst or an initiating system, of at least (i) an optionally substituted vinyl aromatic, (ii) a $C_4$-$C_6$ conjugated diene and/or a $C_{15}$ hydrocarbon, and (iii) the said $C_5$ olefin mixture. The catalyst or catalytic system is preferably a Friedel-Craft catalyst or catalytic system.

A preferred oligomer or polymer is a tackifying resin.

A further advantageous use, according to the second aspect of the invention, is for making an adhesive composition comprising the said tackifying resin and an elastomer.

The optionally substituted vinyl aromatic is preferably chosen among styrene, alpha-methyl-styrene, a vinyl toluene, a vinyl xylene, a vinyl ethyl benzene, a vinyl ethyl toluene, a vinyl ethyl xylene, a vinyl isopropyl toluene, a vinyl isopropyl xylene, and their mixtures, wherein the $C_4$-$C_6$ conjugated diene is selected from 1,3-butadiene, isoprene, piperylene, 1-methyl-cyclopentadiene, 2-methyl-cyclopentadiene, 5-methyl-cyclopentadiene, and wherein the $C_{15}$ hydrocarbon is farnesene, preferably (E)-β-farnesene, and their mixtures and their cis and/or trans isomers. Piperylene and farnesene are preferred.

The oligomer or polymer according to the second aspect of the invention and its above-described embodiments is not hydrogenated or optionally partially or fully hydrogenated.

More preferably, the optionally substituted vinyl aromatic is alpha-methyl-styrene, styrene, or their combination.

When an elastomer is used, it is selected from the group consisting of styrene-isoprene block copolymers, polyacrylate resins, poly ethylene vinyl acetate (EVA) resins, poly styrene butadiene resins, random styrene butadiene (SBR) copolymers, styrene butadiene block copolymers, styrene butadiene styrene (SBS) block copolymers, styrene isoprene butadiene styrene (SIBS) copolymers, styrene ethylene propylene styrene (SEPS) copolymers, styrene ethylene butylene styrene (SEBS) block copolymers, amorphous polyolefin (APO) resins, and mixtures thereof.

The polymer resulting from the use according to the second aspect of the invention has preferably a glass transition temperature Tg above 35° C., a number average molecular mass Mn from 400 to 2400 g/mol, a mass average molecular mass Mw from 900 to 4000 g/mol, a Z-average molecular mass Mz from 1500 to 6000 g/mol, a molecular weight distribution Mw/Mn from 1.50 to 1.90. More preferably, the polymer has a Mn from 600 to 1400, a Mw from 1000 to 2400, and a Mz from 2000 to 4000 g/mol.

The $C_5$ olefin mixture obtained from dehydration of an alcohol mixture, according to the second aspect of the invention, can be used for making a fuel or a fuel additive, especially wherein the $C_5$ olefin mixture further contains diisoamyl ether. Diisoamyl ether, which is an ether resulting from dehydration and condensation of two molecules of a $C_5$ alcohol, was found to have excellent properties as cetane improver since its cetane number is 96, when measured using ASTM D6890 method. Diisoamyl ether is a byproduct of fusel oil dehydration depending on experimental condition, especially depending on reaction temperature and/or catalyst. Experimental conditions may be adapted by the skilled artisan without excessive burden to produce more or less ether products, depending on the final use of the $C_5$ olefin mixture. Another valuable $C_5$ ether suitable for cetane improvement is dipentyl-ether, which cetane number is 111 using ASTM D6890.

The use of $C_5$ ethers obtained from dehydration of fusel oil, as fuel or fuel additive for diesel engine is thus preferred.

According to a third embodiment, the instant invention provides an article comprising a substrate and an adhesive composition resulting from the use according to the second aspect of the invention, applied to at least one part of at least one surface of the substrate, wherein the substrate is selected from the group consisting of a tape, a label, wood, wood composite, woven or non-woven fabric, paper, cardboard, carton, and a book-binding.

According to a fourth embodiment, the instant invention provides a case and carton assembly line comprising an adhesive station, wherein the adhesive station dispenses an adhesive composition resulting from the use according to the second aspect of the invention.

According to a fifth embodiment, the instant invention could be suitable for use as adhesive composition for manufacturing of metal composite material having metal sheets bound together using the said adhesive composition, optionally in the presence of a spacing material between the metal sheets, such as polymer or metal honeycomb. A preferred metal is aluminum, magnesium, titanium, and their alloys with other elements, iron and its alloys with other elements, including stainless steel grades, preferably austenitic, such as AISI/SAE 304, 307, 316, 347 and their variants such as 304H, 304L.

Unless otherwise specified in the present document, percentages are given in percentage by weight.

EXPERIMENTAL

Dehydration Process Conditions. General Procedure:

In examples 1 and 2, $C_5$ alcohols were dehydrated over a $\gamma\text{-Al}_2\text{O}_3$ catalyst. $\gamma\text{-Al}_2\text{O}_3$ catalyst, as pellets of 35-45 mesh (0.500-0.354 μm) is obtained by crushing $\gamma\text{-Al}_2\text{O}_3$, as 1.2 mm extrudates, which exhibit the following textural properties: specific surface area of 200 m²/g, porous distribution centered around 124 Å and porous volume of 0.588 ml/g. A stainless-steel tubular reactor having an internal diameter of 10 mm is loaded with 20 ml of the $\gamma\text{Al}_2\text{O}_3$ catalyst pellets. The void spaces before and after the catalyst are filled with granulated SiC of 0.5 mm.

The temperature profile is monitored with the aid of a thermocouple placed inside the reactor. Reactor temperature is increased at a rate of 60° C./h to 550° C. under 45 NL/h $N_2$ and 10 NL/h air. Once at 550° C., nitrogen flow is then reduced to 30 NL/h. After 30 minutes, nitrogen flow is further reduced to 10 NL/h.

After a further 30 minutes, nitrogen flow is stopped and airflow increased to 20 NL/h. after 1 hour, reactor temperature is then decreased to the temperature of the test and then purged by nitrogen. The nitrogen is then replaced by the $C_5$ alcohols feed (either a pure 3-methylbutan-1-ol feed or raw fusel oil). The catalytic tests are then performed down-flow, at near atmospheric pressure (pressure of 2 barg (bar gauge)), in a temperature range of 300-450° C. and with a weight hour space velocity (WHSV) varying from 2 to 7 h$^{-1}$. Analysis of the products is performed by using an on-line gas chromatograph.

Example 1

3-methylbutan-1-ol dehydration 3-methylbutan-1-ol was fed through a pre-heater and onto the catalyst bed, with an initial internal reactor temperature of 250° C. and an LHSV of 4 hr$^{-1}$. The temperature was then increased by 25° C. at 12 h intervals until 450° C.

Complete alcohol conversion is observed from 325° C. with about 86% of 3-methylbut-1-ene (kinetic isomer) 10% 2-methylbut-2-ene and 3% of 2-methylbut-1-ene. From 375° C., the proportion of 2-methylbut-2-ene (thermodynamic isomer) and/or 2-methylbut-1-ene is observed to be superior to that of 3-methylbut-1-ene. From 400° C., the proportion of 2-methylbut-2-ene is observed to be superior to that of 2-methylbut-1-ene and/or 3-methylbut-1-ene. See, table 1, below for detailed results.

TABLE 1

| LHSV (h$^{-1}$) | 4 | 4 | 4 | 4 | 4 | 4 | 4 | 4 | 4 |
| --- | --- | --- | --- | --- | --- | --- | --- | --- | --- |
| T (° C.) | 250 | 275 | 300 | 325 | 350 | 375 | 400 | 425 | 450 |
| 3MB1 | 2.5 | 5.1 | 56.6 | 86.2 | 63.3 | 38.5 | 9.3 | 4.8 | 4.9 |
| 2MB1 | 0.0 | 0.0 | 0.5 | 3.0 | 9.7 | 17.4 | 27.1 | 29.3 | 28.7 |
| 2MB2 | 0.0 | 0.1 | 2.3 | 10.0 | 26.3 | 43.1 | 62.3 | 63.8 | 60.1 |
| Diisoamyl ether | 76.9 | 35.8 | 13.2 | 0.1 | 0.0 | 0.0 | 0.0 | 0.0 | 0.0 |
| 3MB1-OH | 20.2 | 58.6 | 26.5 | 0.0 | 0.0 | 0.0 | 0.0 | 0.0 | 0.0 |
| others | 0.4 | 0.3 | 0.9 | 0.6 | 0.7 | 1.0 | 1.3 | 2.2 | 6.4 |

3MB1: 3-methylbut-1-ene;
2MB1: 2-methylbut-1-ene;
2MB2: 2-methylbut-2-ene;
3MB1-OH: 3-methylbutan-1-ol Example 2

Fusel Oil Dehydration

A biosourced raw fusel oil feed containing approximately 20.9 wt % ethanol, 1.5 wt % 1-propanol, 0.3 wt 1-butanol, 14.0 wt % isobutanol, 45.6 wt % 3-methylbutan-1-ol, 16.7 wt % 2-methylbutan-1-ol, 0.1 wt % ethyl pentanoate, 0.3 wt % ethyl hexanoate, and higher ethyl esters and pyrazine derivatives, is subjected to dehydration to produce $C_5$ olefins as main constituents.

Following filtration to remove fine particles, fusel oil was fed through a pre-heater and onto the catalyst bed, with an initial internal reactor temperature of 400° C., and an overall feed LHSV of 4 hr$^{-1}$. The temperature was then increased to 425° C. The results are displayed in table 2, below.

TABLE 2

| LHSV (h$^{-1}$) | 4 | 4 |
|---|---|---|
| T (° C.) | 400 | 425 |
| C$_2$ (ethylene) | 16.0 | 10.4 |
| C$_3$ (propylene) | 1.3 | 0.9 |
| C$_4$ (butenes) | 12.2 | 7.3 |
| 3-methylbut-1-ene | 33.2 | 11.9 |
| 2-methylbut-1-ene | 8.9 | 7.9 |
| 2-methylbut-2-ene | 21.0 | 17.9 |
| Higher olefins and others | 7.5 | 43.7 |

Complete alcohol conversion is observed at both temperatures. At 400° C., 3-methylbut-1-ene makes up around 53wt % of isoamylenes. Increasing the temperature to 425° C. resulted in an increased proportion of C$_5$ olefin 2-methylbut-2-ene and to a decreased total isoamylenes yield due to the formation of heavier compounds.

Example 3

Polymers made with C$_5$ Olefins

Seven polymerizations of an aromatic modified aliphatic resin were completed using the various isomers of methylbutene; 2-methylbut-2-ene (2MB2), 2-methylbut-1-ene (2MB1), and 3-methylbut-1-ene (3MB1) along with their mixtures. The resulting resins were characterized by their glass transition temperatures (Tg), color, and molecular weights.

2MB2 was distilled before use. 2MB1 and 3MB1 are essentially pure and were used as purchased. In case C$_5$ olefins originate from fusel oil, appropriate distillation may yield desired C$_5$ olefins or a C$_5$ olefin cut. In this respect, it may be desirable for economical and/or product properties reasons to use a C$_5$ olefin cut comprising C$_4$ olefins and/or C$_6$ olefins.

The polymerization feed comprised piperylene concentrate which was distilled before use, alpha methylstyrene, and branched olefin. The 2MB2 in the base case blend was replaced in kind by the other branched olefins and the branched olefin blends.

The described resins were obtained by the cationic polymerization of feed blends comprising cis- and trans-piperylene, a branched olefin or branched olefin blend, and alpha-methylstyrene. They were conducted by a semi-batch mode in a round-bottom flask equipped with a stirrer and a cold water condenser. The flask was purged with nitrogen for 20 minutes before a heel of 10 g of toluene was added and the reactor temperature was raised to 35° C. using an external jacket. To the well-stirred toluene heel, 0.3 g of anhydrous aluminum chloride powder was added. When the powder was well dispersed, the feed blend was added at a rate of 1.5 mL/min resulting in an exothermic reaction. Subsequent 0.3 g aliquots of aluminum chloride powder were added after 10, 60, 110, and 160 mL of feed had been added over a total period of 110 minutes. When the entire feed blend (approximately 100 g) had been added, the mixture was stirred for an additional 30 minutes at which point the reaction was no longer exothermic. At this time, the catalyst was quenched with the addition of approximately 10 g of anhydrous isopropanol. The clear, yellow solution was then added to approximately 30 g of water in a 250-mL separatory funnel, shaken, and then allowed to separate into organic and aqueous phases. The lower aqueous phase was removed and the organic phase washed twice more with 25% aqueous isopropanol.

The organic phase was then transferred to a 250-mL, 3-neck flask equipped with a thermocouple, a nitrogen purge, and a Dean-Stark trap fitted with a cold water condenser, along with an antioxidant (0.2 wt % on expected resin yield). The flask was heated by means of a heating mantel to a temperature of 230° C. during which time non- and un-reacted components were collected. When the pot temperature reached 230° C., the nitrogen purge was replaced with a steam purge. While maintaining a 230° C. pot temperature, steam condensate was collected along with low molecular weight oligomeric material. When a quantity of steam condensate equal to that of resin yield (approximately 60 g), a nitrogen purge was restored in order to remove the last traces of water. The product resin was obtained as a light yellow molten liquid that solidified upon cooling to afford a clear, friable solid.

Without willing to be bound by a theory, it seems branched olefins, i.e. tri-substituted olefins, are effective chain transfer agents due to the formation of a tertiary cation when incorporated into a growing polymer chain during cationic polymerization. This tertiary cation may add another monomer or, more likely, lose a proton to a monomer thus forming an unsaturated chain end and transferring the polymerization process to a new polymer chain. Both 2MB1 and 2MB2 form more stable tertiary cations than 3MB1. One might assume that 3MB1 under the acidic conditions of Friedel Crafts polymerization, rearrange by proton migration to form 2MB2.

Results of the seven polymerizations carried out that tested the ability of the three branched olefins individually and in combination to control Tg/molecular weight in a typical aromatic modified formulation, are shown in Table 3, below.

Run 1 represents the base case where the only added branched olefin is 2MB2. In runs 2 and 3, 2MB1 and 3MB1 were used in place of 2MB2. Runs 4 through 7 used blends combining 2MB1, 2MB2 and 3MB1. Tg and molecular weight are generally understood to be directly related given a constant resin composition. So while 2MB1 and 2MB2 give similar tertiary cationic intermediates, they give slightly different structures upon adding another monomer (propagation) or proton loss. Polymerization of 2MB1 results in highly substituted carbons adjacent to a methylene carbon whereas polymerization product from 2MB2 contains adjacent methyl groups that hinder rotation about the common bond. Such steric hindrance is believed to increase the energy needed to achieve molecular mobility and results in a slightly higher Tg. This effect is seen in Table 3 where despite the identical molecular weights obtained in Runs 1 and 2, 2MB2 gives a resin with a higher Tg. 3MB1 is likely not as effective in chain transfer as this branched olefin produces a resin having a higher Tg and molecular weight.

Runs 4 through 7 give results that are weighted averages of the effects from the three branched olefins. For each of runs #1 to #7, piperylene, as mixture of cis+trans isomers stands for 30-35 wt % of the total feed blend, and alpha-methyl-styrene stands for 2-6 wt % of the total feed blend. The remaining is the branched olefin composition as specified in Table 3, and a solvent, preferably a stream of olefins and aliphatics that is recovered by distillation from the product resin solution during finishing process.

There was no significant effect of the nature of branched olefin on resin color.

TABLE 3

| Physical properties | | | | | | | | |
|---|---|---|---|---|---|---|---|---|
| | | \multicolumn{7}{c}{Run#} |
| | | 1 | 2 | 3 | 4 | 5 | 6 | 7 |
| Branched olefin | 2MB2 | 8.5 | 0.0 | 0.0 | 2.7 | 4.7 | 5.4 | 6.0 |
| composition (g) | 2MB1 | 0.0 | 8.5 | 0.0 | 1.0 | 1.2 | 2.0 | 2.0 |
| | 3MB1 | 0.0 | 0.0 | 9.9 | 4.8 | 2.6 | 1.1 | 0.6 |
| Glass transition temperature (Tg, ° C.) | | 45.5 | 38.2 | 50.8 | 48.0 | 47.5 | 45.1 | 39.8 |
| Color, G | | 2.4 | 2.3 | 2.4 | 2.2 | 2.3 | 2.2 | 2.3 |
| Molecular weight | Mn | 830 | 792 | 589 | 829 | 824 | 817 | 811 |
| | Mw | 1364 | 1312 | 1618 | 1436 | 1400 | 1361 | 1347 |
| | Mz | 2168 | 2145 | 2961 | 2403 | 2322 | 2210 | 2168 |
| Molecular weight distribution (MWD) | | 1.64 | 1.66 | 1.88 | 1.73 | 1.70 | 1.67 | 1.66 |
| Conversion, % | 2MB2 | 86.0 | 86.8 | 91.7 | 89.2 | 87.7 | 88.3 | 99.4 |
| | 2MB1 | 87.6 | 96.4 | 100.0 | 93.6 | 92.8 | 95.1 | 100.0 |
| | 3MB1 | — | — | 69.9 | 78.8 | 75.9 | 82.3 | 72.8 |

Conversion rates of 2MB1 and 2MB2 are high, generally above 85% whereas the conversion of 3MB1 is somewhat lower. This is likely due to the relatively more stable tertiary cation intermediates that are formed with 2MB1 and 2MB2 versus the less stable secondary cation formed when 3MB1 is incorporated. This is in agreement with the relatively low conversions of 2-pentenes that are generally found as a component of piperylene concentrate.

2MB1, 2MB2, and 3MB1 are each individually and in combination apt to control Tg and molecular weight in the synthesis of a typical aromatic modified resin comprised of piperylene, alpha methylstyrene, and branched olefin.

Unexpectedly, mixtures of 2MB1 and/or 2MB2 comprising significant amounts of 3MB1 were polymerized with high conversion rates, while reaching acceptable molecular weight and MWD, and achieving satisfying Tg.

First alternative dehydration process. General procedure:

In Examples 4 to 6, $C_5$ alcohols were dehydrated over a ferrierite catalyst. A ferrierite catalyst (Zeolyst CP914, powder) was calcined under 50 NL/h $N_2$ at 550° C. for 6 h (1° C./min). The catalyst was then crushed and sieved to 35-45 mesh. 10 mL of catalyst (5.53 g) was loaded, diluted with 10 mL of carborandum (SiC 0.5 mm).

A stainless-steel tubular reactor having an internal diameter of 10 mm is loaded with 10 mL of ferrierite catalyst. The void spaces before and after the catalyst are filled with an equivalent volume of SiC granulated at 0.5 mm. The temperature profile is monitored with the aid of a thermocouple placed inside the reactor. Analysis of the products is performed by using an on-line gas chromatograph.

Reactor temperature was increased at a rate of 60° C./h to 550° C. under 10 NL/h $N_2$. After 1 hour, reactor temperature was then decreased to the temperature of the test and then purged by nitrogen.

Example 4

3-methylbutan-1-ol Dehydration 3-methylbutan-1-ol was fed through a pre-heater and onto the catalyst bed, with an initial internal reactor temperature of 220° C., an LHSV of 8 $hr^{-1}$ and a pressure of 2 barg.

At 220° C. a 3-5% alcohol conversion was observed. Increasing the temperature to 240° C. resulted in only a marginal higher conversion of 4-5%. At 260° C., a 98% conversion was observed with selectivity of 59% towards 2-methylbut-2-ene. At 270° C., conversion increased to >99% and 60% 2-methylbut-2-ene. Selectivity and conversion remained constant for 60h at 270° C. with no signs of catalyst deactivation.

Example 5

2-methylbutan-1-ol Dehydration 2-methylbutan-1-ol was fed through a pre-heater and onto the catalyst bed with an initial internal reactor temperature of 240° C., an LHSV of 8 $hr^{-1}$ and a pressure of 2 barg. At 240° C., a 5-6% alcohol conversion was observed. At 260° C., alcohol conversion increased to 80-85% with selectivity of 59% towards 2-methylbut-2-ene.

Example 6

Distilled Fusel Oil Dehydration

A biosourced distilled fusel oil feed (125-135° C. cut) containing less than 0.1 wt % ethanol, less than 0.1 wt % 1-propanol, less than 0.1 wt % 1-butanol, approximately 1.0 wt % isobutanol, 83.5 wt % 3-methylbutan-1-ol, 13.8 wt % 2-methylbutan-1-ol, less than 0.1 wt % ethyl pentanoate, and higher ethyl esters and pyrazine derivatives, was subjected to dehydration to produce $C_5$ olefins as main constituents, i.e. a C5 olefin mixture according to the invention.

Distilled fusel oil was fed through a pre-heater and onto the catalyst bed with an initial internal reactor temperature of 260° C., an overall feed LHSV of 8 $hr^{-1}$ and a pressure of 2 barg.

The temperature was then increased gradually to 375° C. where a 78% isoamyl alcohol conversion was observed. At 400° C., this conversion increased to >99%, with selectivity of 55% towards 2-methylbut-2-ene. These operating conditions were maintained for 100 h with no perceived loss in selectivity.

Second Alternative Dehydration Process. General Procedure:

In Examples 7 to 9, $C_5$ alcohols were dehydrated over a ferrierite catalyst. A ferrierite catalyst (Zeolyst, CP914 CYL-1.6) as extrudates was crushed and sieved to 35-45 mesh. 10 mL of catalyst (6.26 g) were loaded and diluted with 10 mL of carborandum (SiC 0.5 mm).

A stainless-steel tubular reactor having an internal diameter of 10 mm is loaded with 10 mL of ferrierite catalyst. The void spaces before and after the catalyst are filled with an equivalent volume of SiC granulated at 0.5 mm. The temperature profile is monitored with the aid of a thermocouple placed inside the reactor. Analysis of the products is performed by using an on-line gas chromatograph.

Reactor temperature was increased at a rate of 60° C./h to 550° C. under 10 NL/h $N_2$. After 1 hour, reactor temperature was then decreased to the temperature of the test and then purged by nitrogen.

Example 7

3-methylbutan-1-ol Dehydration 3-methylbutan-1-ol was fed through a pre-heater and onto the catalyst bed with an initial internal reactor temperature of 240° C., an LHSV of 8 hr$^{-1}$ and a pressure of 2 barg.

At 240° C., a 2-3% alcohol conversion was observed. Increasing the temperature to 250° C. resulted in a higher conversion of approximately 20%. At 260° C., a >99% conversion was observed with selectivity of 60-61% towards 2-methylbut-2-ene. Selectivity remained stable for 22 h at 260° C. A 3-methylbutan-1-ol feed with 8% water was then injected and the temperature maintained at 260° C. for 90 h during which selectivity towards 2-methylbut-2-ene remained stable at 60-61% despite formation of 1-2% heavier compounds.

Example 8

2-Methylbutan-1-ol Dehydration 2-methylbutan-1-ol was fed through a pre-heater and onto the catalyst bed with an initial internal reactor temperature of 240° C., an LHSV of 8 hr$^{-1}$ and a pressure of 2 barg.

At 240° C., a 96-98% isoamyl alcohol conversion was observed towards 23-24% 2-methylbut-2-ene and 41-42% trans-2-pentene. At 250° C., the alcohol conversion increased to >99% towards approximately 50% 2-methylbut-2-ene and 24% trans-2-pentene. Increasing the reactor temperature to 260° C. resulted in an increased 2MB2 selectivity around 59%. At 270° C., stable selectivity towards 60% 2MB2 was observed over 10 h.

Example 9

Distilled Fusel Oil Dehydration

A biosourced distilled fusel oil feed (125-135° C. cut) containing less than 0.1 wt % ethanol, less than 0.1 wt % 1-propanol, less than 0.1 wt % 1-butanol, approximately 1.0 wt % isobutanol, 83.5 wt % 3-methylbutan-1-ol, 13.8 wt % 2-methylbutan-1-ol, less than 0.1 wt % ethyl pentanoate, and higher ethyl esters and pyrazine derivatives, was subjected to dehydration to produce $C_5$ olefins as main constituents, i.e. a $C_5$ olefin mixture according to the invention.

Distilled fusel oil was fed through a pre-heater and onto the catalyst bed with an initial internal reactor temperature of 270° C., and an overall feed LHSV of 8 hr$^{-1}$ and a pressure of 2 barg.

The temperature was then increased gradually until desired results were obtained. Initial results at 350° C. showed near complete conversion (<1% alcohol) with 60% selectivity for 2MB2. Temperature increase to 360° C. resulted in 62-63% selectivity, stable for 50h at 360° C. (to 195h on stream). Increased temperature to 380° C. appeared to marginally decrease 2MB2 selectivity in favor of trans-2-pentene and cis-2-pentene.

The invention claimed is:

1. A $C_5$ olefin mixture containing:
 (i) at least 50 wt % of an olefin mixture comprising (i-a) 2-methyl-but-2-ene, (i-b) 2-methyl-but-1-ene and (i-c) 3-methyl-but-1-ene, and
 (ii) (ii-a) one $C_4$ olefin chosen among 1-butene, 2-butene, 2-methylpropene, and/or (ii-b) one C6 olefin chosen among 1-hexene, 2-hexene, 3-hexene, 2-methyl-1-pentene, 3-methyl-1-pentene, 4-methyl-1-pentene, 2-ethyl-1-butene, 2,3-dimethyl-1-butene, 2,3-dimethyl-2-butene, cyclohexene, 2-methyl-2-pentene, 3-methyl-2-pentene, 3,3-dimethyl-1-butene, 1-methyl-cyclopentene, 3-methyl-cyclopentene, 4-methyl-cyclopentene, methylene-cyclopentane,
 the $C_5$ olefin mixture optionally comprising (ii-c) one $C_{15}$ hydrocarbon,
 the $C_5$ olefin mixture being obtained by a process comprising the steps of:
 a) providing an initial composition comprising at least 20 wt % of a $C_5$ branched alcohol based on the total weight of the initial composition, and
 b1) dehydrating the initial composition and separating the obtained dehydrated composition to provide a first stream enriched in $C_2$ olefins, a second stream enriched in $C_5$ olefins, and a third stream containing heavier compounds, the $C_5$ olefin mixture being recovered from the second stream enriched in $C_5$ olefins, or
 b2) separating the initial composition to provide a first stream enriched in $C_2$ alcohols, a second stream enriched in $C_5$ alcohols, and a third stream enriched in heavier compounds, and dehydrating the second stream enriched in $C_5$ alcohols to obtain the $C_5$ olefin mixture,
 wherein the initial composition is obtained by fermentation of biomass feedstocks, and
 wherein the initial composition comprises at least 20 wt % Cs branched alcohol, at least 1 wt % ethanol, at least 0.1 wt % n-propanol, at least 1 wt % $C_4$ alcohols, at most 1.5 wt % esters and at least 5 wt % water, based on the total weight of the initial composition.

2. The $C_5$ olefin mixture according to claim 1, further comprising (i-d) cis-2-pentene and/or trans-2-pentene.

3. The $C_5$ olefin mixture according to claim 1, wherein the branched alcohol is isoamyl alcohol.

4. The $C_5$ olefin mixture according to claim 1, wherein the biomass feedstock is raw or refined fusel oil.

5. The $C_5$ olefin mixture according to claim 1, wherein the dehydration step is carried out in the presence of a dehydration catalyst, containing at least one of (a) zeolites, (b) alumina, (c) silica-alumina, and (d) alumino silicate or any mixture thereof.

6. A process for the preparation of the $C_5$ olefin mixture according to claim 1,
 comprising the steps of:
 a) providing an initial composition comprising at least 20 wt % of a $C_5$ branched alcohol based on the total weight of the initial composition, and
 b1) dehydrating the initial composition and separating the obtained dehydrated composition to provide a first stream enriched in $C_2$ olefins, a second stream enriched in $C_5$ olefins, and a third stream containing heavier compounds, the $C_5$ olefin mixture being recovered from the second stream enriched in $C_5$ olefins, or
 b2) separating the initial composition to provide a first stream enriched in $C_2$ alcohols, a second stream enriched in $C_5$ alcohols, and a third stream enriched in heavier compounds, and dehydrating the second stream enriched in $C_5$ alcohols to obtain the $C_5$ olefin mixture, wherein the initial composition is obtained by fermentation of biomass feedstocks.

7. The process according to claim 6, wherein the $C_5$ olefin mixture further comprises (i-d) cis-2-pentene and/or trans-2-pentene.

8. The process according to claim 6, wherein the $C_5$ branched alcohol is isoamyl alcohol.

9. The process according to claim 6, wherein the initial composition comprises at least 20 wt % $C_5$ branched alcohol, at least 1 wt % ethanol, at least 0.1 wt % n-propanol, at least 1 wt % $C_4$ alcohols, at most 1.5wt % esters and at least 5 wt % water, based on the total weight of the initial composition.

10. The process according to claim 6, wherein the biomass feedstocks are raw or refined fusel oil.

11. The process according to claim 10, wherein the feedstocks are a $C_{4+}$ or $C_4$-$C_6$ cut isolated from fusel oil.

12. The process according to claim 6, wherein the dehydration step is carried out in the presence of a dehydration catalyst, containing at least one of (a) zeolites, (b) alumina, (c) silica-alumina, and (d) alumino silicate or any mixture thereof.

13. The process according to claim 12, wherein the zeolites have the MFI, MTT, FER, MEL, TON, MWW, EUO, or MFS structure.

14. The process according to claim 12, wherein the dehydration catalyst is chosen from gamma-alumina, H-ZSM-5, H-FER, ZSM-5 containing phosphorous or any mixture thereof.

15. The process according to claim 6, wherein the initial composition is obtained by fermentation of feedstocks by microalgae or microorganisms.

16. A process for making an oligomer or a polymer, said process comprising:
combining, in the presence of a catalyst or an initiating system, at least (i) an optionally substituted vinyl aromatic, (ii) a $C_4$-$C_6$ conjugated diene and/or a $C_{15}$ hydrocarbon, and (iii) the $C_5$ olefin mixture according to claim 1.

17. The process according to claim 16, for making an adhesive composition comprising a tackifying resin and an elastomer and/or a polyolefin, the tackifying resin being the oligomer or polymer.

18. The process according to claim 17, wherein the elastomer is selected from the group consisting of styrene-isoprene block copolymers, polyacrylate resins, poly ethylene vinyl acetate (EVA) resins, poly styrene butadiene resins, random styrene butadiene (SBR) copolymers, styrene butadiene block copolymers, styrene butadiene styrene (SBS) block copolymers, styrene isoprene butadiene styrene (SIBS) copolymers, styrene ethylene propylene styrene (SEPS) copolymers, styrene ethylene butylene styrene (SEBS) block copolymers, amorphous polyolefin (APO) resins, and mixtures thereof.

19. The process according to claim 16, wherein the optionally substituted vinyl aromatic is chosen among styrene, alpha-methyl-styrene, a vinyl toluene, a vinyl xylene, a vinyl ethyl benzene, a vinyl ethyl toluene, a vinyl ethyl xylene, a vinyl isopropyl toluene, a vinyl isopropyl xylene, and their mixtures, wherein the $C_4$-$C_6$ conjugated diene is selected from 1,3-butadiene, isoprene, piperylene, 1-methyl-cyclopentadiene, 2-methyl-cyclopentadiene, 5-methyl-cyclopentadiene, and wherein the $C_{15}$ hydrocarbon is farnesene, and their mixtures and their cis and/or trans isomers, and wherein the oligomer or polymer is not hydrogenated, partially hydrogenated or fully hydrogenated.

20. The process according to claim 16, wherein the polymer has a glass transition temperature Tg above 35° C., a number average molecular mass Mn from 400 to 2400 g/mol, a mass average molecular mass Mw from 900 to 4000 g/mol, a Z-average molecular mass Mz from 1500 to 6000 g/mol, a molecular weight distribution Mw/Mn from 1.50 to 1.90.

21. The process according to claim 16, wherein the oligomer or polymer is a tackifying resin.

22. A process for making a fuel or fuel additive, said process comprising:
conducting the process of claim 6,
wherein the $C_5$ olefin mixture contains diisoamyl ether.

* * * * *